United States Patent
Mollenauer et al.

[11] Patent Number: 6,032,671
[45] Date of Patent: Mar. 7, 2000

[54] METHOD AND APPARATUS FOR COMBINED DISSECTION AND RETRACTION

[75] Inventors: Kenneth H. Mollenauer, Los Gatos; James E. Jervis, Atherton, both of Calif.

[73] Assignee: General Surgical Innovations, Inc., Palo Alto, Calif.

[21] Appl. No.: 09/093,102

[22] Filed: Jun. 8, 1998

Related U.S. Application Data

[63] Continuation of application No. 08/619,902, Mar. 20, 1996, abandoned.

[51] Int. Cl.[7] .................................................. A61B 19/00
[52] U.S. Cl. ......................................... 128/896; 600/201
[58] Field of Search .................................... 600/201, 116, 600/18, 205, 204, 207, 214; 128/898; 606/192, 194, 190, 1; 604/96, 101; 623/1

[56] References Cited

U.S. PATENT DOCUMENTS

| | | |
|---|---|---|
| 4,148,307 | 4/1979 | Utsugi . |
| 4,651,717 | 3/1987 | Jakubczak ........................ 623/8 X |
| 4,990,139 | 2/1991 | Jang . |
| 5,163,949 | 11/1992 | Bonutti . |
| 5,176,619 | 1/1993 | Segalowitz . |
| 5,197,971 | 3/1993 | Bonutti . |
| 5,295,994 | 3/1994 | Bonutti . |
| 5,308,327 | 5/1994 | Heaven . |
| 5,309,896 | 5/1994 | Moll et al. . |
| 5,313,962 | 5/1994 | Obenchain ........................ 606/1 X |
| 5,318,586 | 6/1994 | Ereren . |
| 5,331,975 | 7/1994 | Bonutti . |
| 5,345,927 | 9/1994 | Bonutti . |
| 5,387,235 | 2/1995 | Chuter . |
| 5,413,558 | 5/1995 | Paradis . |
| 5,425,357 | 6/1995 | Moll et al. . |
| 5,437,638 | 8/1995 | Bowman . |
| 5,454,365 | 10/1995 | Bonutti . |
| 5,505,702 | 4/1996 | Arney . |
| 5,514,153 | 5/1996 | Bonutti . |
| 5,520,609 | 5/1996 | Moll et al. . |
| 5,527,355 | 6/1996 | Ahn . |
| 5,540,711 | 7/1996 | Kieturakis et al. ............. 600/204 X |
| 5,607,441 | 3/1997 | Sierocuk et al. . |
| 5,620,457 | 4/1997 | Pinchasik et al. . |
| 5,632,761 | 5/1997 | Smith et al. .................... 600/207 X |
| 5,690,668 | 11/1997 | Fogarty et al. .................. 600/207 X |

FOREIGN PATENT DOCUMENTS

| | | |
|---|---|---|
| 0573273 | 12/1993 | European Pat. Off. . |
| WO 95/32663 | 12/1995 | WIPO . |
| WO96/00531 | 1/1996 | WIPO . |
| WO96/00597 | 1/1996 | WIPO . |

*Primary Examiner*—Mickey Yu
*Assistant Examiner*—Kelly O'Hara
*Attorney, Agent, or Firm*—Lyon & Lyon LLP

[57] ABSTRACT

A method and apparatus for dissecting a first layer of tissue from a second layer of tissue and thereafter holding open an anatomic space for the performance of a surgical procedure. The method includes steps of making an incision in a body, introducing a deflated balloon dissector into the incision, inflating the balloon dissector to effect dissection of the first layer of tissue from the second layer of tissue, deploying a retractor within the anatomic space in order to hold open the anatomic space, and optionally deflating or evacuating the balloon dissector to open a cavity for surgical manipulations. The apparatus includes a combined dissector-retractor having a balloon retractor disposed upon the surface of the balloon dissector and integrated therewith.

12 Claims, 8 Drawing Sheets

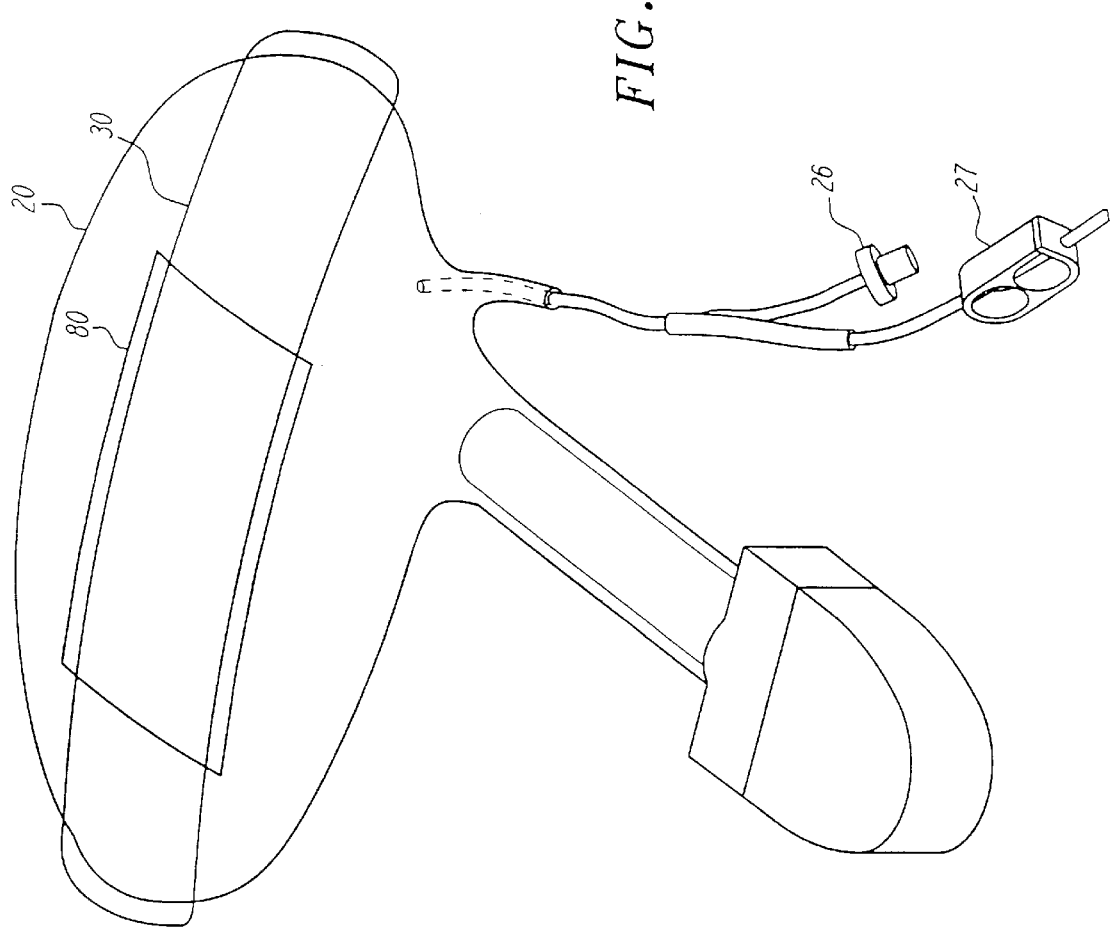

METHOD AND APPARATUS FOR COMBINED DISSECTION AND RETRACTION

This is a continuation of application Ser. No. 08/619,902 filed Mar. 20, 1996 now abandoned.

FIELD OF THE INVENTION

The invention relates to tissue dissectors and tissue retractors for use in the field of surgery. More particularly, the invention relates to a combined dissector-retractor and methods of dissection-retraction to create an anatomic space by using combined or independent dissector-retractor apparatus.

BACKGROUND OF THE INVENTION

Current methods used for retracting tissue and improving visualization and working space include mechanical separation using metal retractors during surgery, balloon retractors, and direct pressure of an unconfined flow of fluid such as water or $CO_2$ during surgery. A number of retractors have been disclosed and, in the interest of brevity, will not be further described here. The reader is referred to Bonutti, U.S. Pat. No. 5,197,971, Bonutti, U.S. Pat. No. 5,295,994, Bonutti, U.S. Pat. No. 5,345,927, and Moll et al., U.S. Pat. No. 5,309,896, these and all other references cited in this document are expressly incorporated by reference as if fully set forth herein in their entirety. Tissue dissection has also been discussed and, for general considerations, the reader is referred to Bonutti, U.S. Pat. No. 5,163,949, Kieturakis, International Publication No. WO95/32663, Kieturakis et al., EP 0,573,273 A2, published Dec. 8, 1993, Kieturakis et al., International Publications No. WO96/00531, published Jan. 11, 1996, and Fogarty et al., International Publication No. WO96/00597, published Jan. 11, 1996.

Tissue retractors have been particularly useful in orthopedic surgery. There are several orthopedic procedures which have the potential to offer both low cost and patient benefit. Among these is spinal fusion. There are about 200,000 such procedures performed annually in the United States. In general, the procedure is performed to eliminate a ruptured vertebral disk which is causing significant patient discomfort, and subsequently to promote fusion between the then-exposed and adjacent vertebra. This fusion can be promoted by any of several proprietary prosthetic systems or by traditional bone prostheses, or by a combination of the two. Most traditional systems have utilized a posterior approach to the spine.

Several newer systems, some currently under investigation have utilized an anterior approach, and seem to promise better clinical results. The open anterior approach is highly invasive, however, and has led researchers to try a transperitoneal laparoscopic variation to the open procedure. This is an improvement, but still subjects the patient to those same risks associated with invasion of the peritoneum outlined above, but if anything, more severely.

There have recently been several cadaver studies where an extraperitoneal laparoscopic approach to the lumbar spine has been attempted with success. This is a natural target procedure since the dissected space required is essentially the same as that required for aortic reconstruction. Most interesting is that the space dissection requirements are largely the same for all of the prosthetic systems under study.

SUMMARY OF THE INVENTION

We have discovered that tissue dissection in combination with retraction can be an important component of the surgical and, particularly, the vascular and orthopedic armamentarium. In many procedures, it would be convenient to provide retraction in the space created by tissue dissection during the course of the subsequent procedure. In balloon dissection, the dissection is performed by a flexible bladder which is inflated in order to create a predetermined space. Once inflated, the bladder generally occupies the extremities of that space. By providing on the surface of this main bladder, a subsidiary bladder or bladders, a secondary inflatable structure can be created which can be activated and serve as a retractor. This secondary bladder can be inflated before or after the primary dissecting balloon is deflated or partially deflated. If necessary, the primary bladder may be evacuated in order to keep it out of the way in the operating space or, once the secondary structure is positioned, the primary bladder integrity may be sacrificed. The secondary structure can be completely contained on or within the surface of the primary dissection bladder, or it may extend beyond the limits of the primary bladder.

One specific instance where this sort of device would be particularly useful is in retroperitoneal access to the lumbar spine, vena cava, and/or aorta and related structures. Balloon dissection in this area can be used to free the peritoneum from the floor of the abdomen, extending up toward or beyond the kidneys, and crossing the midline of the abdomen. The entry incision is advantageously lateral and just above the iliac crest, but may be elsewhere. In the process of this dissection, the peritoneum and contents are lifted superiorly such that they are out of the way of the desired access to the lumbar/aortic space, be it from the anterior midline or from a more lateral approach. The main balloon then fills the space created and, on deflation, the peritoneum and contents return to their normal position. Trendelenburg or other patient positioning can have some beneficial effect, but generally not enough to maintain the desired access. Retraction is desirable. This retraction can be provided by a secondary structure on the primary balloon surface which is inflated and left inflated during the procedure. After the procedure has been completed, the entirety of the bladder may be removed.

In another embodiment, an inflatable structure can be provided which, in concert with the adjacent tissue, provides or tends to provide a space into which surgical instruments can be introduced for purposes of visualization or therapy. In this embodiment, the operating space is between the balloon and the tissue. Depending on tissue behavior and balloon shape, the space may be open, as by "tenting," or may require that the resilience of the balloon-tissue interface accommodate insertion of the instruments. One procedure where this sort of embodiment would be useful is in treatment of carpal tunnel syndrome where space is very limited, but some tenting will occur given adjacent dilation by means of the balloon dissector-retractor.

In another embodiment, the dissector-retractor of the invention is used to gain access to the aorta for repair of an aortic aneurysm. Vascular grafts have been used endoluminally to repair the interior lumen of the aorta as a therapy for aortic aneurysm. However, in certain cases, the aorta will further expand to form a still larger aneurysm and effectively bypass the vascular graft. Therefore, in another embodiment of the present invention, a dissector-retractor is used to create space in which a "banding" procedure, whereby an external repair is effected around the aorta. Such a repair would provide a radial force in an inward direction.

BRIEF DESCRIPTION OF DRAWINGS

Further features of the present invention will become apparent to those skilled in the art to which the present invention relates from reading the following specification with reference to the accompanying drawings, in which:

FIG. 2 depicts a dissector-retractor apparatus in accordance with an alternate embodiment and capable of uncoupling;

DETAILED DESCRIPTION OF THE INVENTION

Figure 1:
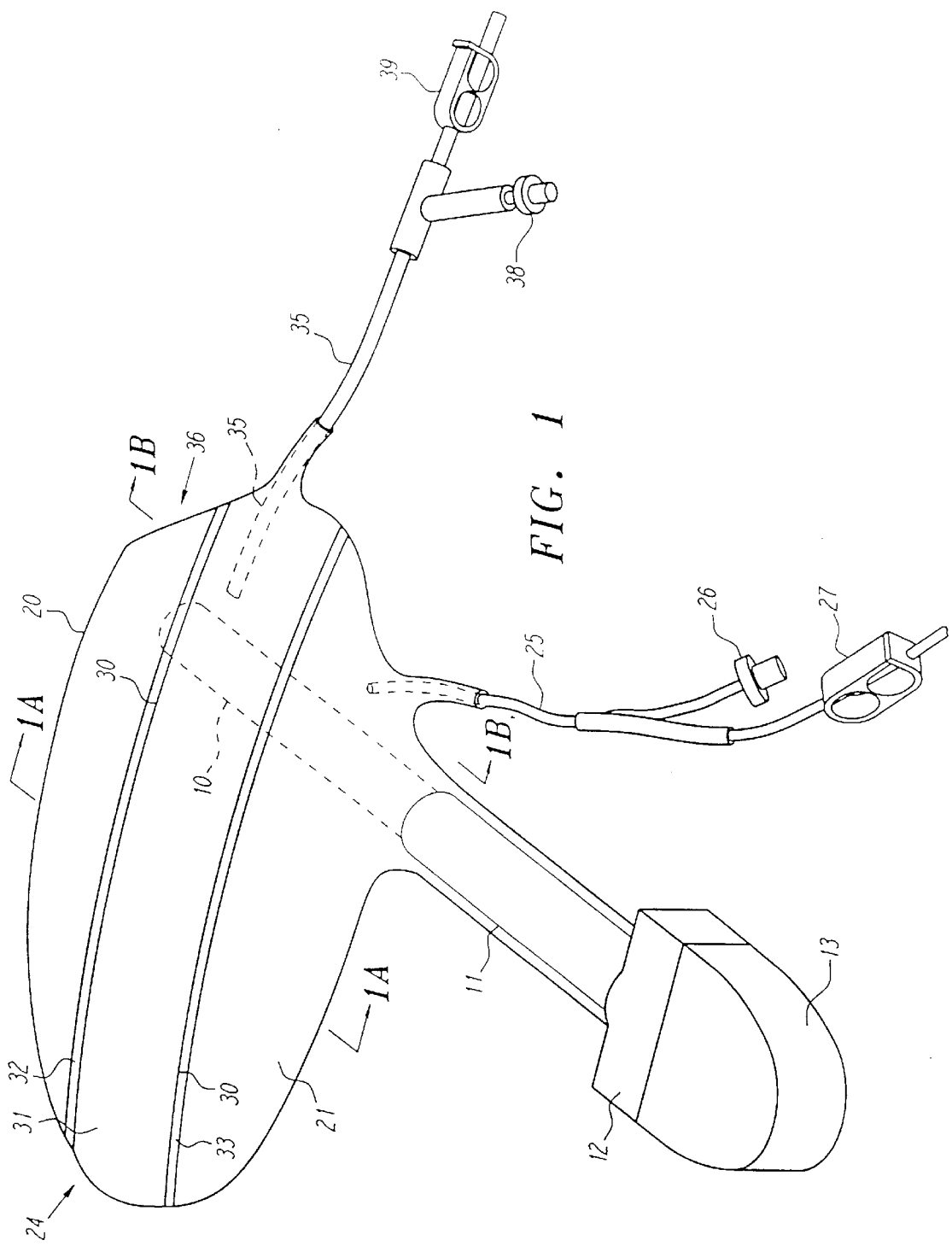
FIG. 1 depicts a combined dissector-retractor apparatus.

A combination dissector-retractor as disclosed herein is depicted in FIG. 1. The dissector 20 comprises a first flexible wall 21 which is joined at its outer edge with a second flexible wall directly subjacent wall 21 and hidden from view in FIG. 1. The first and second walls are joined at a seam and define a first inflatable chamber which is in fluid communication with inflation port 25. Inflation port 25 branches, with one port terminating in one-way valve 26 which is connectable to an inflation bulb (not shown), and the other port serving as a deflation port and having a pinch clamp 27 disposed thereon. Dissection balloon 20 is connected to first handle 12 which may include optional tube 11. Tunneling member 10 and second handle 13 are slidably mounted through the lumen of first handle 12 and optional tube 11. Tunneling member 10 is optionally transparent and hollow in order to facilitate insertion of an endoscope to advantageously provide visualization of the procedure and device usage. The design and construction of tunneling members, as well as there use with balloon expanders, is well known in the art and will not be further discussed here in the interest of brevity.

Referring again to FIG. 1, the dissector includes on one surface the balloon retractor 30 which comprises flexible wall 31 having edges 32 and 33 which are joined at a first seam and a second seam with flexible wall 21 of dissector 20. Flexible walls 31 and 21 define a second inflatable chamber which is in fluid communication with inflation port 35, and is inflatable independently of the first inflatable chamber. Inflation port 35 branches, with one port terminating in one-way valve 38 which is connectable to an inflation bulb (not shown), and the other port serving as a deflation port and having a pinch clamp 39 disposed thereon.

Figure 1B:
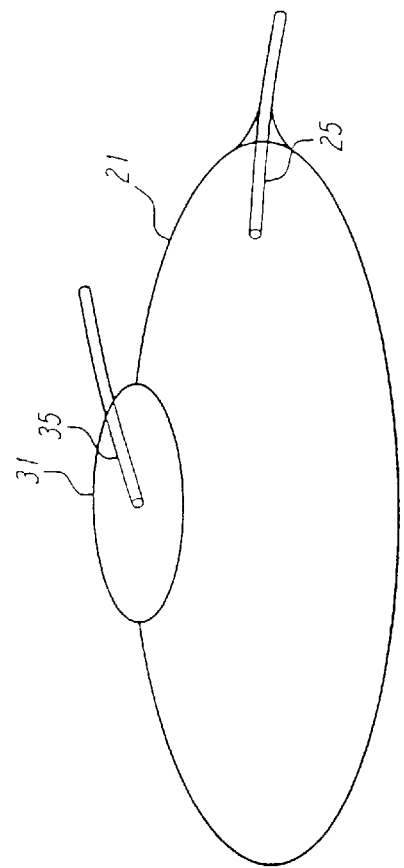
FIG. 1B depicts a cross-sectional view of the combined dissector-retractor of FIG. 1 taken through section line B—B.
Figure 1A:
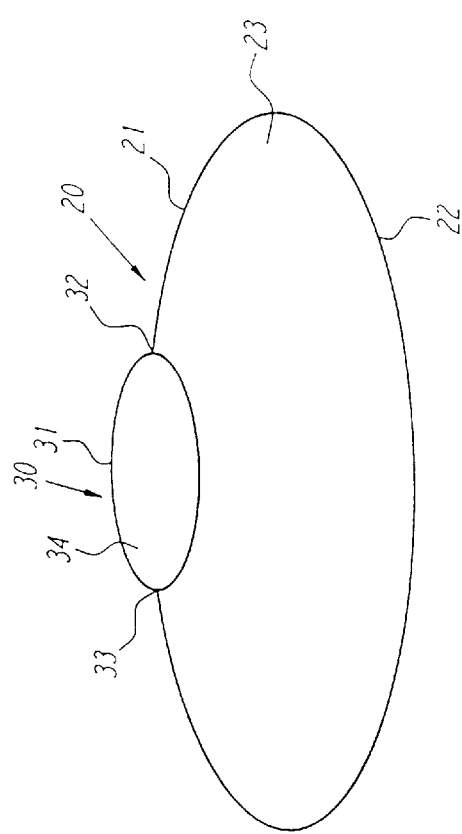
FIG. 1A depicts a cross-sectional view of the combined dissector-retractor of FIG. 1 taken through section line A—A.

FIG. 1A depicts a cross-sectional view through section line A—A of the combined dissector-retractor of FIG. 1. The dissector 20 comprises a first flexible wall 21 which is joined to a second flexible wall 22, and these walls together define inflatable chamber 23. Disposed on the surface of flexible wall 21 is balloon retractor 30 which comprises flexible wall 31 joined to wall 21 at edges 32 and 33. Walls 31 and 21 define a second chamber 34 which is inflatable independently of chamber 23.

FIG. 1B depicts a cross-sectional view through section line B—B of the combined dissector-retractor of FIG. 1. The components shown in FIG. 1B are the same as described with reference to FIG. 1A, with the exceptions that FIG. 1B also shows inflation ports 25 and 35 which are in fluid communication with the balloon dissector and retractor, respectively.

Bladder pressure is a significant parameter to consider in connection with tissue dissection, tissue expansion, and tissue retraction in accordance with methods and apparatus described herein. Tissue expansion requires the lowest pressures, typically around 18 mm Hg to avoid collapse of the venous system and tissue necrosis. More generally, tissue expansion can be conducted at a pressure of 10 mm Hg, more preferably 12 mm Hg, more preferably 14 mm Hg, more preferably 16 mm Hg, more preferably 18 mm Hg, more preferably 20 mm Hg, more preferably 22 mm Hg, and more preferably 24 mm Hg. Cell formation and tissue distention try to accommodate applied stress over time, increasing tissue area.

Inter-planar soft tissue dissection can be conducted at about 3 psi, or 150 mm Hg pressure in order to progress, and is typically in the range of about 100–300 mm Hg. More generally, tissue dissection can be conducted at a pressure of 100 mm Hg, more preferably 110 mm Hg, more preferably 120 mm Hg, more preferably 130 mm Hg, more preferably 140 mm Hg, more preferably 150 mm Hg, more preferably 160 mm Hg, more preferably 170 mm Hg, more preferably 180 mm Hg, more preferably 200 mm Hg, more preferably 250 mm Hg, and even up to about 300 mm Hg and above. Specific pressure requirements for tissue dissection may depend on space, geometry, and the nature of the tissue to be dissected. Short term, there is little danger of necrosis, but some danger of tissue rupture is present if sufficient force is applied.

Tissue retraction by inflatable devices is more complicated. If pressure is determined by tissue resistance, the force or pressure will vary with the nature of the structure being moved and the extent of tissue translation and rotation desired. There is some concern for necrosis as retraction is of intermediate duration, but a large area of inflatable retractor-tissue contact will mitigate local pressures applied. If pressure requirements are determined by device geometry in order to produce structural stability and the forces required, then the pressures may be independent of tissue resistance. Inflatable balloon retractors can be made to conform to tissue morphology unlike hard surfaced mechanical retractors.

Balloon dissectors and retractors can be made from a number of materials well known in the art, including elastomers, inelastic materials, and high performance materials, e.g., Kevlar. Elastomers in practical thicknesses for inflatable laparoscopic devices generally exhibit a very brief Hookian region, then a long, essentially horizontal plateau in their stress-strain characteristics. Therefore, in use when external applied loads are seldom hydrostatic, expansion will usually proceed along the path of least resistance, thinning the wall locally, and perhaps progressing to rupture of the bladder. In addition, fabrication methods often produce enough variability in wall thickness and/or blemishes, that there is usually a great tendency to inflate via local aneurysm even without applied load, or to rupture under localized strain, particularly if the blemish coincides with an area of considerable strain. Predefined elastomeric balloon shapes can generally be obtained only if one only operates within or near the Hookian region of the stress-strain curve, but this necessitates either thick or hard walls, or a combination. These are generally less desirable characteristics in inflatable medical devices. When stress is removed, these materials generally recover essentially all strain immediately or within a brief time.

Inelastic materials also have stress-strain characteristics which start with a generally Hookian region followed by what might be termed a plateau. Bladder parameter combinations are available which have desirable thickness and softness characteristics, yet can easily attain 150 mm Hg or greater. Therefore, shapes in practical devices can be reliably maintained up to pressures which will dissect. Further inflation causes some distortion, but changes in shape as size increases only occur slowly. Removal of stress causes strain recovery, but more slowly and less completely than with elastomers. Balloons made of such inelastic materials as polyurethane are currently manufactured by General Surgical Innovations, Inc. (Palo Alto, Calif.). The major distinction between these materials is the pressure at which the plateau starts given the thickness and hardness parameter ranges of practical devices.

There are also high performance materials which have either innate stress-strain characteristics with high strength and low elongation, e.g., Kevlar, or acquire these characteristics through fabrication, perhaps incurring a high degree of biaxial orientation (polyester or polyethylene films). These sorts of films are commonly used where great structural rigidity is desired in the inflated bladder. A typical example is an angioplasty balloon. Generally, if great rigidity is required, re-entrant shapes are impractical, although if intermediate rigidity is desired, then some compromises in shape might be possible. Some forms of retractors may fall in these areas.

Tissue retractors hold tissue apart to reveal underlying structures. There are several different kinds of inflatables which can perform retractor functions. One is essentially a dissector left in place to perform retraction in the sense of maintaining the space dissected. In some instances, they are used without insufflation for gasless laparoscopy, but there are other instances in which they might be used in addition to insufflation. In these devices, the inflatable bladder essentially fills the space dissected, but may consist of highly shaped devices in order to provide working access through the dissected space. This may be a combination dissector-retractor, but need not be. The pressure range to dissect may be quite different from that required to retract, indeed the dissection chamber may not be the same as the retraction chamber.

Another sort of retractor is an inflatable structural member like a balloon trocar where the inflatable does not occupy the entire dissected space. The pressure inside the inflatable needs only address the structural requirements of the device. The shape of the device is used to address the allowable unit pressure on the tissue. For example, a simple inflatable cylindrical strut might be used to spread the tissue edges apart. The area of the end of the strut can be sized to protect the tissue from necrosis, but the force required to spread the tissues must be generated within the pressure within the strut, and the strut design must accommodate this pressure. Still another similar device is the dissector of Heaven, U.S. Pat. No. 5,308,327. This device has an internal pressure which is independent of tissue dissection pressures (about 150 mm Hg). It only serves the rigidity of the device when used as a wand to dissect local structures.

In still further alternative embodiments, the retractor may be a piece of malleable metal or similar structure, as depicted in FIG. 2. It may be introduced with the balloon or introduced subsequent to balloon inflation and deployed for retraction purposes. If carried by the balloon structure, it may be housed in pocket 80, at least partially on the surface of the balloon. Likewise, the retractor may be a separate inflatable structure at least partially carried in pocket 80 formed on the surface of the primary balloon, or detachably conveyed by other means, or it may be a separate element.

Referring again to FIG. 1, before use, the combined dissector-retractor balloon apparatus is rolled and/or inverted (folded inwardly) around tunneling member 10 in order to achieve a compact diameter for insertion through an incision. Region 24 of dissector 20 can be rolled toward tunneling member 10, and region 36 can be rolled toward tunneling member 10 in a similar manner to reduce the diameter. In an alternative embodiment, region 24 will be folded inwardly, or inverted, toward tunneling member 10, and optionally past this member until region 24 passes into region 36. Then, region 36, which contains a portion of region 24, is rolled toward tunneling member 10 and the remainder of region 24 extending to the left of tunneling member 10 can optionally be rolled toward tunneling member 10. This embodiment, which includes inverting as well as rolling, permits "staged dissection." In use, when the balloon dissector is inflated, region 36 first unrolls, and simultaneously region 24 unrolls. As region 36 expands, it becomes engaged against the iliac crest, and thereafter serves as an anchor for the entire device as further tissue dissection occurs. Next, region 24 expands, and thereby reverts, expanding to the left as depicted in FIG. 1. Staged dissection may be advantageous because it takes advantage of relative strengths of tissues to control the direction of dissection by using certain anatomic structures as an anchor, and in certain circumstances, it facilitates visualization.

Figure 3:
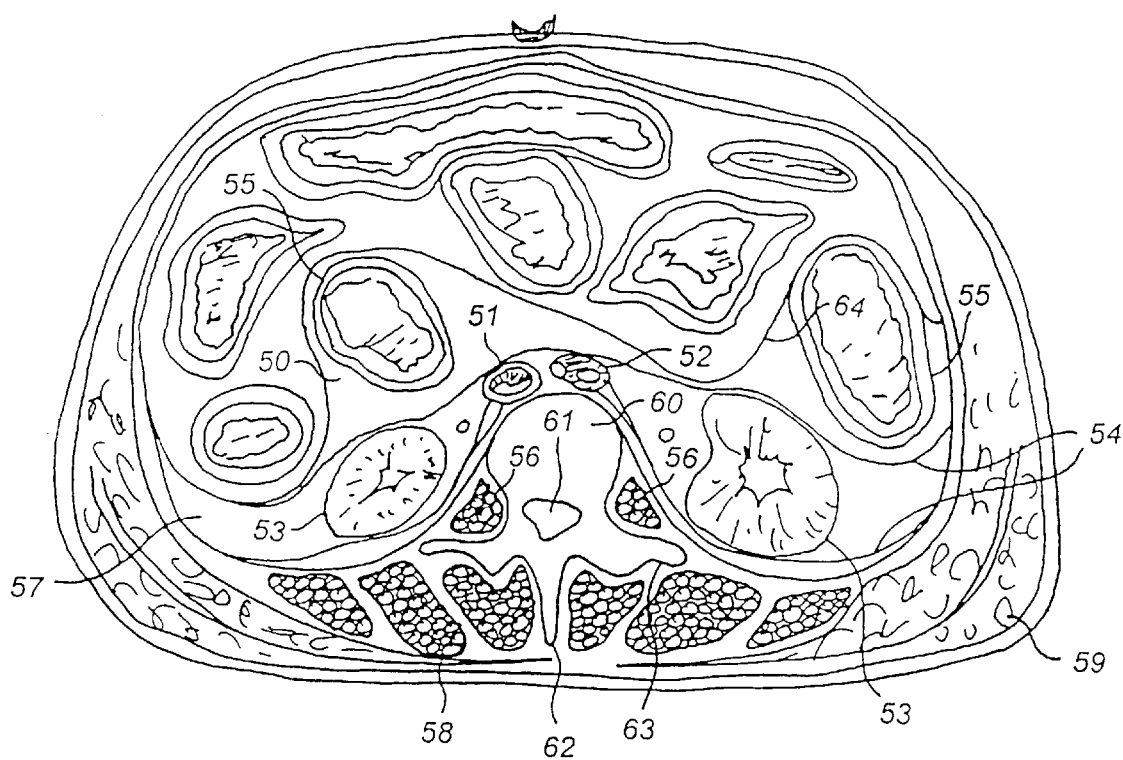
FIG. 3 is a cross-sectional view of the abdomen intersecting the kidneys and showing the peritoneal cavity and retroperitoneal space.
Figure 4:
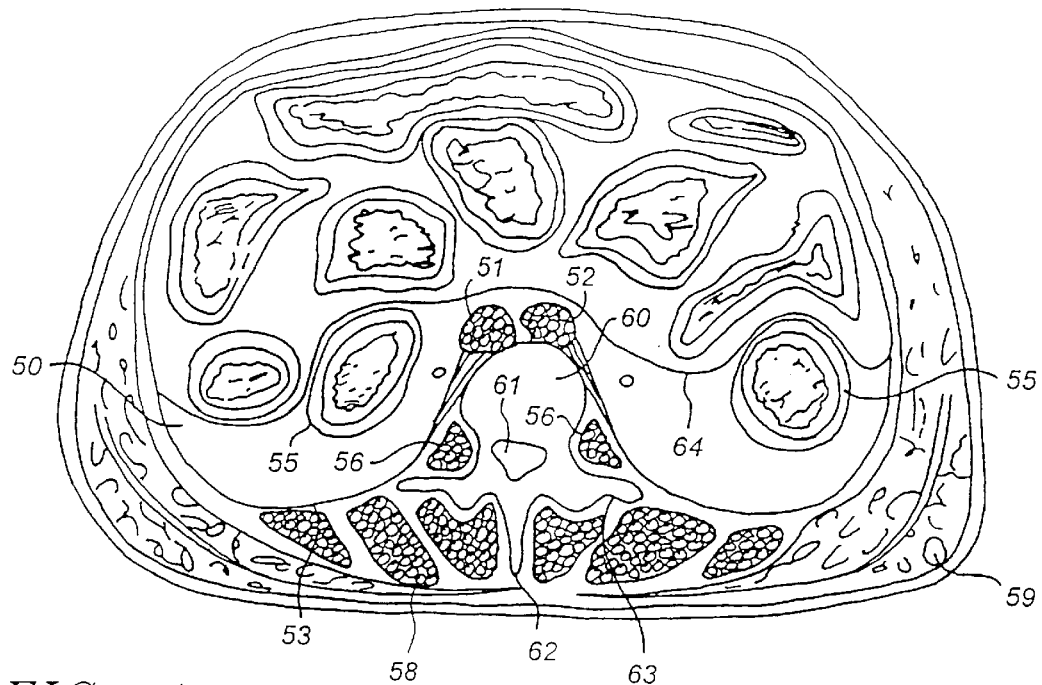
FIG. 4 is a cross-sectional view of the abdomen inferior to the kidneys and showing the peritoneal cavity and retroperitoneal.

In use, the combined dissector-retractor can access the retroperitoneal space to create a cavity which permits surgical procedures on the spine, aorta, vena cava, kidneys, adrenal glands, lymph nodes, ureters, iliaci, iliac vessels, and other organs accessible from the retroperitoneal space and known to those skilled in the art. FIG. 3 depicts a cross-sectional view of the abdomen, showing the peritoneum 64, anterior retroperitoneal space 50, aorta 51, vena cava 52, kidneys 53, anterior and posterior renal fasciae 54, colon 55, psoas muscle 56, perinephric space 57, muscle 58, fat 59, and vertebrae 60 having spinal canal 61, spinous process 62, and transverse process 63. FIG. 4 provides a similar illustration, except of a cross-section inferior to the kidneys.

The retroperitoneal approach starts with an insertion which is lateral, usually on the left side just above the iliac crest and below the costal structure (ribs). The tunneling member is inserted and passes through the abdominal fat and muscle, as well as the abdominal fasciae, and then behind the peritoneum, and is advanced toward the spine taking care to avoid the aorta and vena cava which lie just anterior of the spine. The tunneling member carries a balloon apparatus as described above. Once in place in the retroperitoneal space, the balloon dissector is expanded to dissect the peritoneum from the pelvic floor, posterior structures, and superiorly from the renal fasciae. Tissue dissection as described in Bonutti, U.S. Pat. No. 5,163,949, will occur to separate the peritoneum along a natural tissue plane from adjacent tissues. Dissection in this manner will create an anatomic, retroperitoneal space.

Figure 5:
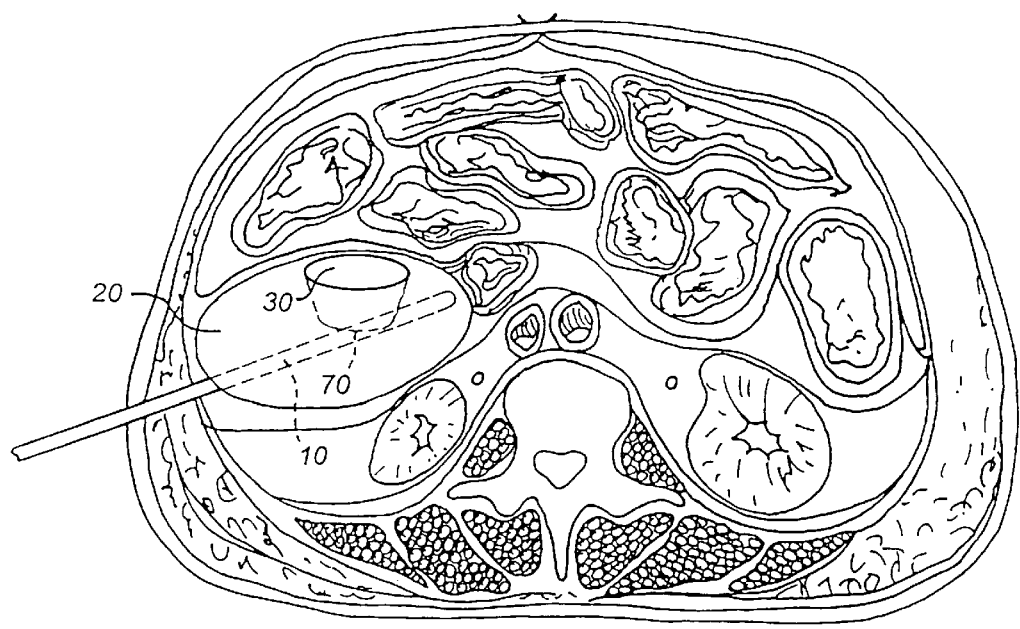
FIG. 5 is a cross-sectional view of the abdomen intersecting the kidneys and showing the deployment of a combined balloon dissector-retractor operably disposed about the distal region of a tunneling member.
Figure 6:
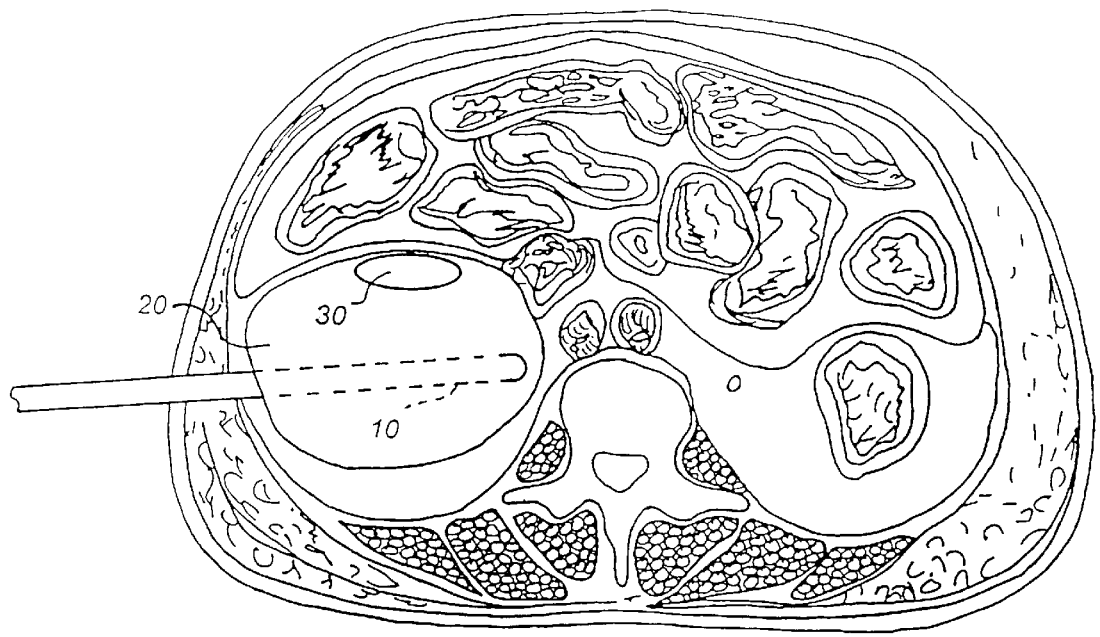
FIG. 6 is a cross-sectional view of the abdomen inferior the kidneys and showing the deployment of a combined dissector-retractor.

FIG. 5 illustrates a combined dissector-retractor used in this manner from a cross-sectional view intersecting the kidneys. FIG. 6 provides a similar illustration, except of a cross-section inferior to the kidneys. With reference to FIG. 5, tunneling member 40 is inserted through a lateral incision below the ribs and above the iliac crest, and balloon dissector 20 is inflated. Tissue dissection will generally begin in the retroperitoneal space in the vicinity of the tunneling member 10 just superior to the iliac crest and inferior to the left kidney, if the incision is on the left side of the body. If staged dissection is used, then, with reference to FIG. 1, region 36 of dissection balloon 20 will inflate first and become anchored against the iliac crest. Next, region 24 will revert and/or unroll in a superior direction and toward the left kidney. With reference to FIG. 5, if region 24 of dissector 20 is rolled about or up to tunneling member 40 in a right-handed manner, or clockwise, as viewed from the right of FIG. 5, then unrolling will tend to result in tissue dissection anterior the renal fasciae and will dissect the peritoneum from the anterior renal fasciae as depicted in FIG. 5. Alternatively, if dissector 20 is rolled about or up to tunneling member 40 in a left-handed manner, or counterclockwise, then unrolling will result in tissue dissection posterior the renal fasciae and therefore posterior the left kidney, not shown. Of course, the same principles apply if entry is made from the right side of the body rather than from the left, but everything is reversed. Deployment of the dissector as described above is then followed by inflation of retractor 30. Once the retractor is deployed, it will hold the peritoneal organs in place even after the balloon dissector is deflated.

Figure 7:
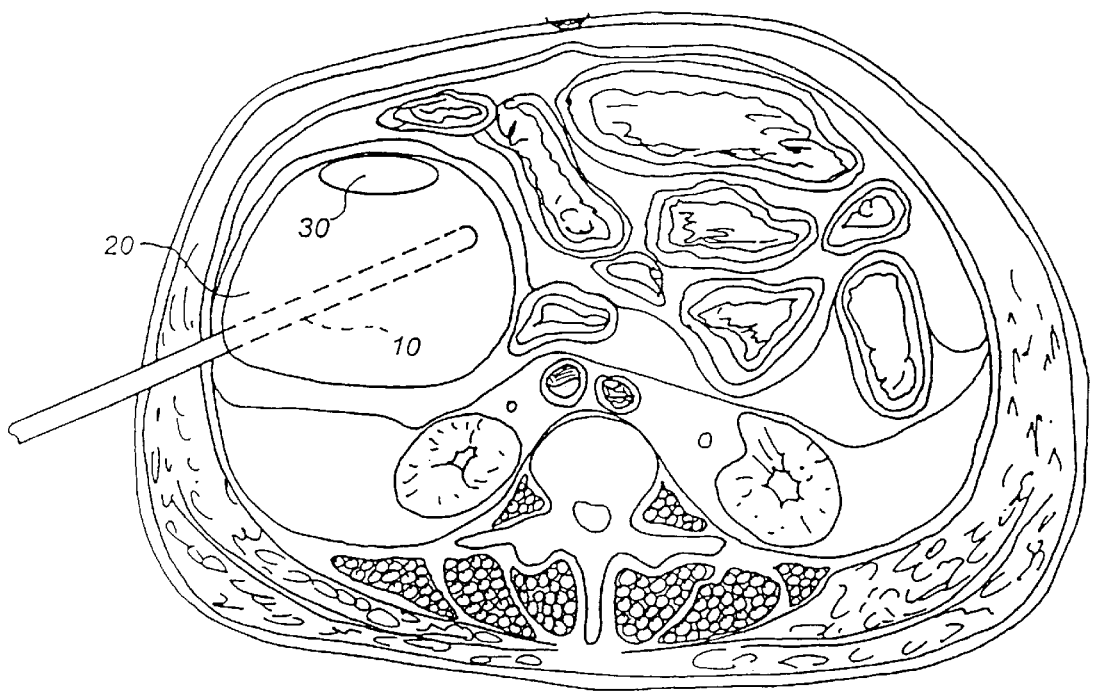
FIG. 7 is a cross-sectional view of the abdomen intersecting the kidneys and showing further expansion of the balloon dissector in order to displace the organs of the peritoneal cavity to the right side of the abdomen in order to facilitate an anterior surgical approach to the lumbar spine.

In certain embodiments, the expansion of the balloon dissection in the left side of the retroperitoneal space pushes the peritoneum and organs bound thereto completely or almost completely laterally to the right side of the person undergoing surgery, as depicted in FIG. 7, and thereby compresses the intestines and peritoneum within the right half of the abdominal cavity. FIG. 7 illustrates tunneling member 40, balloon dissector 20, and retractor 30 inserted behind and pressing against the peritoneum from within the retroperitoneal space. Of course, when the dissector is employed on the right side, organs and peritoneum will be pushed to the left. This repositioning of organs and peritoneum allows access to the spine and organs proximal thereto by way of an anterior approach, i.e., inferior to the umbilicus, without traversing and puncturing the peritoneum.

Figure 8:
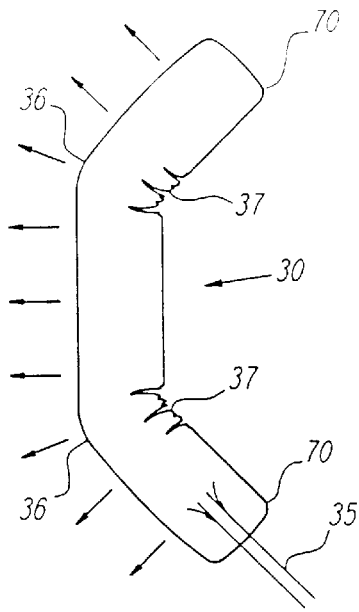
FIG. 8 depicts a secondary balloon retractor structure as viewed from its side in the fully expanded condition.

Either during or after tissue dissection, and sometimes even before dissection, a retractor as described above is deployed. As shown in FIG. 5, the retractor is typically oriented anteriorly in the retroperitoneal space. When the retractor is a balloon, the balloon is inflated and thereby fully extends into the anatomic space created by tissue dissection. Lengthwise extension of the retractor is generally constrained by anatomic structures within the abdominal cavity, and therefore the retractor will assume an arcuate shape, much like a banana when the retractor is extended by inflation. FIG. 8 depicts a balloon retractor 30 in its expanded condition after inflation through port 35. Due to space constraints, the retractor is unable to fully extend to a regular cylindrical volume, but instead assumes a bent shape. The regions of greatest curvature 36 are characterized by wrinkling or folding at segments 37, and terminate at ends 70 as an innermost edge. As the retractor 30 expands, it gains strength and exerts force, pushing tissues outward and to the left as shown by the series of arrows at the left side of retractor 30. This force enables the retractor to hold the peritoneum in place and maintain the retroperitoneal space in an expanded condition for the performance of a surgical procedure therein.

The surgical procedure can begin either before or after deflating and/or removing the balloon dissector. In certain embodiments, the dissector balloon is deflated by releasing its internal pressure, or evacuated by drawing a vacuum on the inflation port to the dissector. Deflation or evacuation of the dissector prior to surgery in the retroperitoneal space is recognized as a preferred embodiment because, while the retractor holds open the retroperitoneal space, the shrinking and/or withdrawal of the balloon dissector opens a cavity for the surgical procedure to be performed without interference from the balloon dissector or other structures associated with the dissector-retractor combination. In this way, surgical access is created to the spine for repairing a vertebral disk, and to other organs proximal to the retroperitoneal space including but not limited to the aorta, vena cava, kidneys, adrenal glands, lymph nodes, ureters, iliaci, etc.

Although the discussion above has dealt primarily with balloon dissection followed by retraction, and then by deflating or evacuating the balloon dissector to create a cavity or working area for a surgical procedure, it should be noted that a number of other options following dissection can be used to advantage and are the subject of alternative embodiments. For example, the dissector can be deflated before retraction occurs. In another embodiment, the dissector and retractor are uncoupled, and the dissector can be deflated and removed before the retractor is deployed and an operation is performed. In another embodiment, the dissector is deflated and removed, followed by insufflation to hold open an anatomic space, and then either endoscopic observation or a surgical procedure is performed. In another embodiment, the dissector is deflated and removed, and then the surgeon switches to an open procedure by further incising and operating. In still another embodiment, the surgeon may diagnose by performing endoscopic observation within the space. In still another embodiment, the balloon dissector is left in place, and the surgeon either operates or observes through windows in the balloon. This may be done from within the pressurized chamber. Alternatively, the balloon dissector is left in place, and the surgeon operates or conducts observation around the balloon. Alternatively, the surgeon can view through the balloon and operate around it, or view around the balloon and operate through it. In still another embodiment, the balloon dissector is deflated, advanced, and re-inflated to progressively open a larger space, and this procedure can be repeated as necessary until the anatomic space thus opened is as large as desired, or reaches the desired location within the body.

Figure 9:
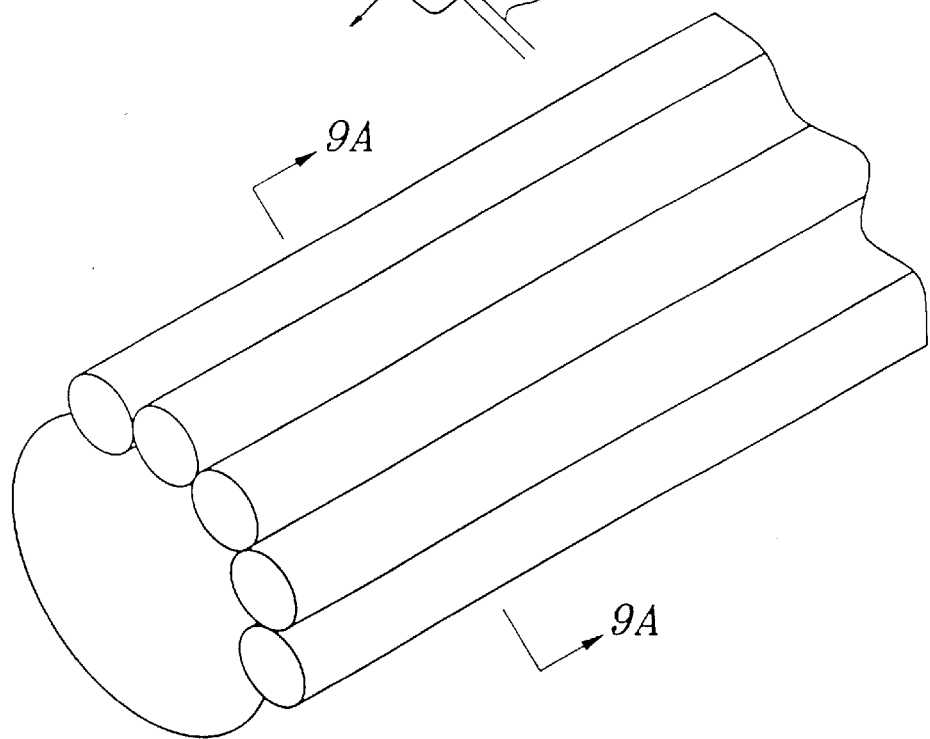
FIG. 9 depicts a combined dissector-retractor adapted for use in vascular surgery.
Figure 9A:
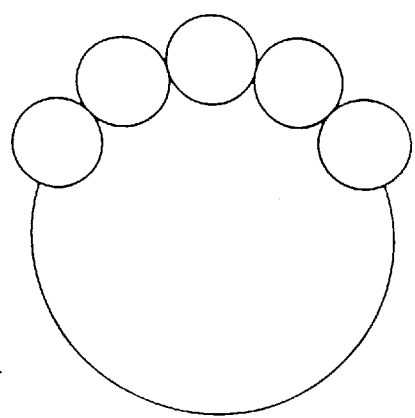
FIG. 9A depicts a cross-sectional view of the combined dissector-retractor of FIG. 9 taken through section line A—A.
Figure 10:
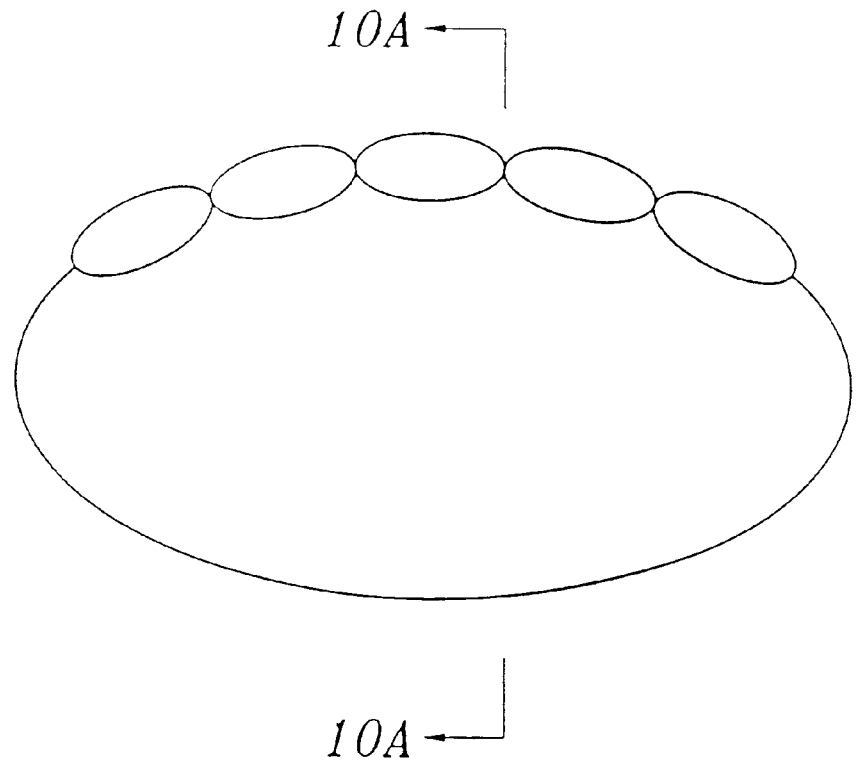
FIG. 10 depicts a combined dissector-retractor adapted for use in breast surgery.
Figure 10A:
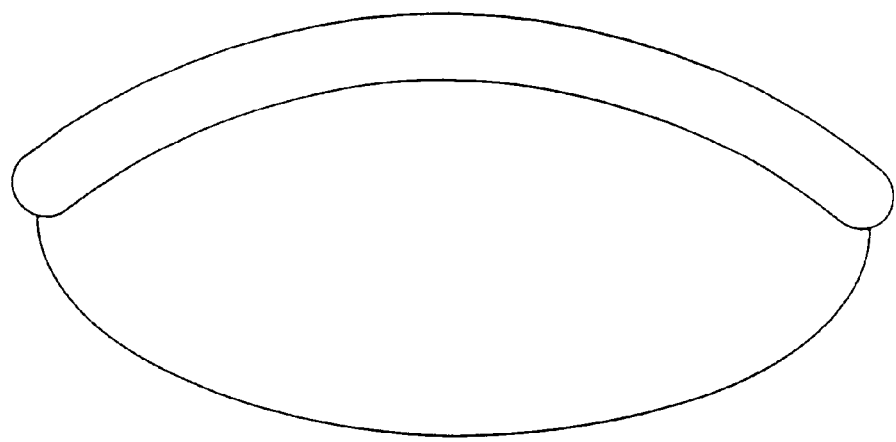
FIG. 10A depicts a cross-sectional view of the combined dissector-retractor of FIG. 10 taken through section line A—A.

Moreover, although the discussion above has been directed to the use of a combined dissector-retractor for access to the retroperitoneal space, it is important to note that this is only one of many potential uses for the dissector-retractor apparatus and procedures disclosed herein. Other uses include vascular surgery for which an elongate cylindrical Fogarty-type balloon dissector can be used with a series of parallel elongate balloons disposed over a 180° segment of such dissector, as depicted in FIGS. 9 and 9A. The procedure of use includes the steps of inserting the combined dissector-retractor through an incision, positioning the dissector in close proximity to a vessel, expanding the dissector to dissect tissue, expanding one or more retractor balloons, and optionally deflating the dissector to open an elongate cavity for a procedure on the vessel. Still another use includes breast augmentation surgery, for which a generally spherical or ellipsoidal balloon dissector can be used with a sequence of short, parallel sausage-like balloons disposed on one face thereof, as depicted in FIGS. 10 and 10A. The procedure of use is as described above for vascular surgery, with the optional additional steps of conducting cautery within the cavity thus created in order to stop bleeding, or further dissecting manually. In still another procedure, the combined dissector-retractor apparatus disclosed herein can be used in place of, or to assist with insufflation.

Thus, while the invention has been described in connection with what are presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A method for dissecting a first layer of tissue from a second layer of tissue and for holding open an anatomic space for the performance of a surgical procedure, the method comprising the steps of:

making an incision in a body;

introducing a combination tissue dissector and retractor apparatus into the incision, said apparatus comprising a deflated balloon dissector having an inflation port and a first flexible wall and a second flexible wall which enclose a chamber, and a deflated balloon retractor disposed on an exterior surface of said balloon dissector along one of said first and second flexible walls, said balloon retractor in its inflated state having a longitudinal centerline which is substantially arcuate;

inflating said balloon dissector, wherein the first layer of tissue is dissected from the second layer of tissue, thereby creating the anatomic space;

inflating said inflatable retractor thereby retracting the anatomic space so that at least a portion of said anatomic space is held open; and deflating at least a portion of the balloon dissector wherein an open cavity is created for the performance of a surgical procedure.

2. The method of claim 1 further comprising the step of inserting surgical instruments around said retractor and into said open cavity.

3. The method of claim 1 wherein the step of deflating said balloon dissector is performed before the step of inflating said balloon retractor.

4. The method of claim 1 wherein said balloon retractor comprises a plurality of parallel inflatable chambers.

5. The method of claim 4 wherein said plurality of inflatable chambers are adapted to be selectively and independently inflatable.

6. The method of claim 5 wherein the step of retracting within the anatomic space is performed by selectively inflating said plurality of inflatable chambers.

7. The method of claim 1, wherein the incision provides access to a retroperitoneal space.

8. The method of claim 7 further comprising the step of performing a surgical procedure on a part of the anatomy selected from the group consisting of the spine, aorta, vena cava, kidneys, lymph nodes, ureters, iliaci, iliac vessels, and adrenal gland.

9. The method of claim 8 further comprising the step of banding the aorta in the region of an endoluminal graft to repair an aortic aneurysm.

10. The method of claim 1, wherein the step of inflating said balloon dissector includes the step of unrolling the balloon dissector.

11. The method of claim 1, wherein the step of inflating said balloon dissector includes the step of reverting the balloon dissector.

12. The method of claim 8 further comprising the step of banding the aorta in the region of an endoluminal graft to prevent bypass of said endoluminal graft.

* * * * *